United States Patent [19]

Shibuya et al.

[11] 4,258,195
[45] Mar. 24, 1981

[54] NOVEL THIOL ESTERS AND PROCESS FOR PREPARING CEPHALOSPORIN COMPOUNDS USING SAME

[75] Inventors: Chisei Shibuya; Kunihiko Ishii; Takumi Sano; Torao Ishida, all of Fuji, Japan

[73] Assignee: Asahi Kasei Kogyo Kabushiki Kaisha, Osaka, Japan

[21] Appl. No.: 18,755

[22] Filed: Mar. 8, 1979

[30] Foreign Application Priority Data

Mar. 9, 1978 [JP] Japan .................................. 53/25975

[51] Int. Cl.³ .................. A01N 43/82; A61K 31/425; C07D 417/12; C07D 501/56
[52] U.S. Cl. .................. 548/136; 260/207.1; 424/246; 424/270; 544/27; 546/170; 546/276; 548/105; 548/110; 548/112
[58] Field of Search .................... 260/302 H; 548/136

[56] References Cited

U.S. PATENT DOCUMENTS

| | | | |
|---|---|---|---|
| 3,278,531 | 10/1966 | Cox et al. | 544/16 |
| 3,516,997 | 6/1970 | Takano et al. | 544/27 |
| 4,107,168 | 8/1978 | Okorodudu | 260/302 SD |

FOREIGN PATENT DOCUMENTS

| | | | |
|---|---|---|---|
| 7105150 | 2/1971 | Japan | 424/246 |
| 7135751 | 10/1971 | Japan | 424/246 |

OTHER PUBLICATIONS

Kurita et al., Chem. Abstracts, vol. 75, Abstract No. 20420p (1971).
Takano et al., Chem. Abstacts, vol. 76, Abstract No. 14563s (1972).
Bison et al., Chem. Abstracts, vol. 83, Abstract No. 58836g (1975).

*Primary Examiner*—Alton D. Rollins
*Attorney, Agent, or Firm*—Finnegan, Henderson, Farabow, Garrett & Dunner

[57] ABSTRACT

An 1,3,4-thiadiazole-5-thiol ester of the formula,

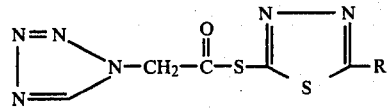

wherein R is a hydrogen atom or a methyl group, a process for their preparation and a process for preparing a cephalosporin compound of the formula,

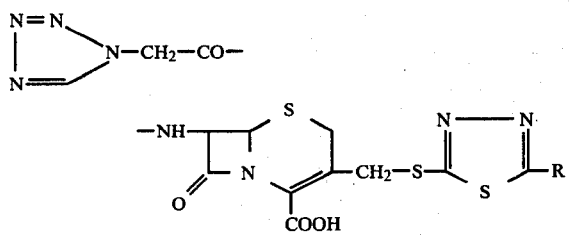

wherein R is the same as defined above, using the above described 1,3,4-thiadiazole-5-thiol ester.

3 Claims, No Drawings

NOVEL THIOL ESTERS AND PROCESS FOR PREPARING CEPHALOSPORIN COMPOUNDS USING SAME

BACKGROUND OF THE INVENTION

1. Field of the Invention

This invention relates to a novel thiol ester having utility as a sleep-inducing agent, an antibacterial agent and an acylating agent for amines and hydrazines, particularly as active esters for preparing cephalosporin compounds, a process for their preparation and a process for the preparation of cephalosporin compounds using the thiol esters.

2. Description of the Prior Art

An 1,3,4-thiadiazole-5-thiol ester of the formula,

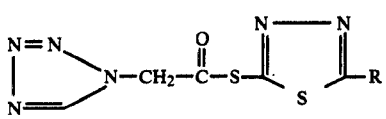

wherein R is a hydrogen atom or a methyl group, and a process for its preparation have not been reported yet.

Further, heretofore, any method is not known for preparing a cephalosporin compound of the formula,

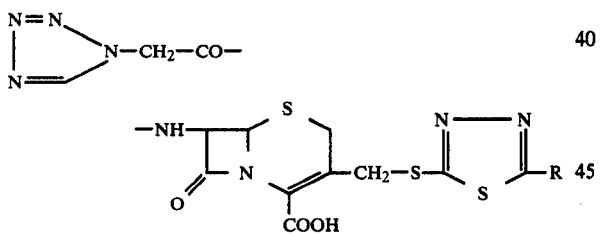

wherein R is a hydrogen atom or a methyl group, by one step using 7-aminocephalosporanic acid or its derivative as the starting material. In order to obtain the above described cephalosporin compound, it is necessary to employ the methods as described in U.S. Pat. Nos. 3,278,531 and 3,516,997, Japanese Patent Publication Nos. 5150/1971 and 35751/1971 as a combination. For example, the above described cephalosporin compound may be prepared by two steps, i.e., either by firstly reacting 7-aminocephalosporanic acid with 1H-tetrazole1-acetic acid and secondly reacting the 7-(1H-tetrazol-1-ylacetamido)cephalosporanic acid thus obtained with an 1,3,4-thiadiazole-5-thiol or by firstly reacting 7-aminocephalosporanic acid with an 1,3,4-thiadiazole-5-thiol and secondly reacting the 7-amino-3-(1,3,4-thiadiazol-5-yl)thiomethyl-3-cephem-4-carboxylic acid thus obtained with 1H-tetrazole1-acetic acid. Thus, these methods require two-step operation, and further a separation procedure such as an extraction with a solvent for recovering the unstable product formed in the first step and, as a result, the yield is too low for practical purposes.

SUMMARY OF THE INVENTION

Accordingly, the present invention in one embodiment provides an 1,3,4-thiadiazole-5-thiol ester of the formula,

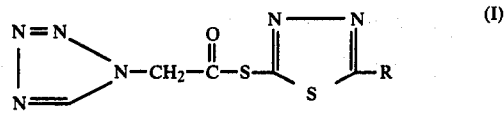

wherein R is a hydrogen atom or a methyl group.

The present invention in another embodiment provides a process for preparing the above described compound of Formula (I).

In a further embodiment, the invention provides a process for preparing a cephalosporin compound of the formula,

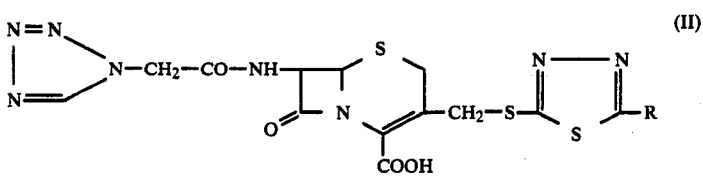

wherein R is the same as defined above, which comprises reacting 7-aminocephalosporanic acid or its derivative with the above described compound of Formula (I).

DETAILED DESCRIPTION OF THE INVENTION

The 1,3,4-thiadiazole-5-thiol esters of Formula (I) of this invention are 1H-tetrazole-1-acetic acid 1,3,4-thiadiazol-5-ylthiol ester and 1H-tetrazole-1-acetic acid 2-metyl-1,3,4-thiadiazol-5-ylthiol ester.

These compounds of Formula (I) of this invention as such are novel compounds and useful as sleep-inducing agents and antibacterial agents of high value.

More specifically, the compounds of Formula (I) of this invention have been found to exhibit an anesthetic effect, i.e., a sleep-inducing effect according to the following experiment.

Male ddY-strain mice aged 7 or 6 weeks, each group consisting of 8 animals, were given an intravenous injection of 35 mg/Kg of sodium thiopental, an anesthetic period of time, i.e., a period of loss of righting-reflex was measured as the anesthetic effect. As a test drug, 1H-tetrazole-1-acetic acid 2-methyl-1,3,4-thiadiazol-5-ylthiol ester was dissolved in dimethyl sulfoxide and the test drug thus prepared was orally administered to the animals at a rate of 0.05 ml/10 g weight one hour before the administration of sodium thiopental. The results are shown in Table below.

TABLE

| Compound | Amount of Administration (P.O.) (mg/Kg) | Period of Time of Anesthesia (Average Value) (minutes) |
|---|---|---|
| 1H-Tetrazole-1-acetic acid 2-methyl-1,3,4-thiadiazol-5-ylthiol ester | 400 | 33.8 |
| 1H-Tetrazole-1-acetic acid | | |

TABLE-continued

| Compound | Amount of Administration (P.O.) (mg/Kg) | Period of Time of Anesthesia (Average Value) (minutes) |
| --- | --- | --- |
| 2-methyl-1,3,4-thiadiazol-5-ylthiol ester | | |
| 1H-Tetrazole-1-acetic acid | 200 | 21.0 |
| 2-methyl-1,3,4-thiadiazol-5-ylthiol ester | 100 | 10.3 |
| Comparative Group | 0 | 8.4 |

As is clear seen from Table as described above, the period of time of anesthesia of 1H-tetrazole-1-acetic acid 2-methyl-1,3,4-thiadiazol-5-ylthiol ester used in an amount of 400 mg/Kg is 4.02 times greater than that of the comparative group. Thus, the prolongation effect on the period of time of anesthesia according to the compounds of Formula (I) of this invention is remarkable.

Also, 1H-tetrazole-1-acetic acid 2-methyl-1,3,4-thiadiazol-5-ylthiol ester of this invention had a minimum inhibitory concentration of 50 μg/mg to *Corynebacterium diphtheriae* P.W. 8 as the antibacterial activity.

Furthermore, the 1,3,4-thiadiazole-5-thiol esters of Formula (I) of this invention are useful as acylating agents for amines and hydrazines, particularly as active esters of preparing cephalosporin compounds.

The 1,3,4-thiadiazole-5-thiol esters of Formula (I) of this invention can be prepared by reacting an 1,3,4-thiadiazole-5-thiol of the formula,

(III)

wherein R is a hydrogen atom or a methyl group, or its derivative with 1H-tetrazole-1-acetic acid or its derivative.

The derivatives of the 1,3,4-thiadiazole-5-thiols which can be employed in this invention include the salts of an alkali metal such as sodium and potassium; the reaction products of a trialkylaluminum such as trimethylaluminum and triethylaluminum; the silyl derivatives such as the trimethylsilyl derivative and the triethylsilyl derivative; and the trifluoroacetates. The 1,3,4-thiadiazole-5-thiols also exist in the form of the 1,3,4-thiadiazole-5-thiones or as a mixture with the 1,3,4-thiadiazole-5-thiones, and are equivalent to the 1,3,4-thiadiazole-5-thiones or the mixture which are accordingly included, as equivalents, in the 1,3,4-thiadiazole-5-thiols of this invention.

The derivatives of the carboxylic group in the 1H-tetrazole-1acetic acid which can be employed in this invention include the acid halides, the acid anhydride, the mixed acid anhydrides, the acid amides, the esters, the acid azides and the nitrile.

Specific examples of suitable derivatives include the acid chloride; the mixed acid anhydrides of a dialkylphosphoric acid such as dimethylphosphoric acid and diethylphosphoric acid, phenylphosphoric acid, diphenylphosphoric acid, dibenzylphosphoric acid, a halogenated phosphoric acid such as chlorophosphoric acid and bromophosphoric acid, a dialkylphosphorous acid such as dimethylphosphorous acid and diethylphosphorous acid, sulfurous acid, thiosulfuric acid, sulfuric acid, an alkylcarbonic acid such as methylcarbonic acid and ethylcarbonic acid, an aliphatic carboxylic acid such as pivalic acid, pentanoic acid, isopentanoic acid, 2-ethylbutanoic acid, trichloroacetic acid and trifluoroacetic acid, an aromatic carboxylic acid such as benzoic acid or the symmetric acid of the 1H-tetrazole-1-acetic acid; the acid amides of imidazole, an 4-substituted imidazole such as 4-methylimidazole and 4-ethylimidazole, dimethylpyrazole, triazole, tetrazole, ammonia, methylamine, dimethylamine; the esters such as methyl ester, ethyl ester, cyanomethyl ester, methoxymethyl ester, vinyl ester, propargyl ester, p-nitrophenyl ester, 2,4-dinitrophenyl ester, trichlorophenyl ester, pentachlorophenyl ester, methanesulfonylphenyl ester, phenylazophenyl ester, phenyl ester, phenylthioester, p-nitrophenylthioester, 2,4-dinitrophenylthioester, p-cresylthioester, carboxymethylthioester, pyranyl ester, pyridyl ester, 8-quinolylthioester, the ester of N,N-dimethylhydroxylamine, 1-hydroxy-2-(1H)-pyridone, N-hydroxysuccinimide or N-hydroxyphthalimide.

The amount of the 1,3,4-thiadiazole-5-thiol of Formula (III) or its derivative which can be employed for the preparation of the 1,3,4-thiadiazole-5-thiol esters of Formula (I) of this invention typically ranges from about 0.5 moles to about 2 moles, and preferably from about 0.9 moles to about 1.2 moles, per mole of 1H-tetrazole-1-acetic acid or its derivative.

When free 1H-tetrazole-1-acetic acid is used, it is necessary to employ a dehydrating agent for condensation.

Appropriate dehydrating agents for condensation which can be employed in this invention include N,N-dicyclohexylcarbodiimide, N,N'-diisopropylcarbodiimide, N-cyclohexyl-N'-morpholinoethylcarbodiimide, N-cyclohexyl-N'-(4-diethylaminocyclohexyl)carbodiimide, N,N'-diethyl-carbodiimide, N-ethyl-N'-(3-dimethylaminopropyl)carbodiimide, N,N'-carbonyldi(2-methylimidazole), pentamethyleneketene-N-cyclohexylimine, diphenylketene-N-cyclohexylimine, an alkoxyacetylene such as methoxyacetylene and ethoxyacetylene, an 1-alkoxy-1-chloroethylene such as 1-methoxy-1-chloroethylene and 1-ethoxy-1-chloroethylene, a trialkyl phosphite such as trimethyl phosphite and triethyl phosphite, ethyl polyphosphates, isopropyl polyphosphate, phosphorus oxychloride, thionyl chloride, oxalyl chloride, triphenylphosphine, 2-ethyl-7-hydroxybenzisoxazolium salt, 2-ethyl-5-m-sulfophenylisoxazolium hydroxide inner salt, (chloromethylene)dimethylammonium chloride, $SO_3$-hexamethylphosphoramide, $SO_3$-N,N-dimethylformamide, sulfonates, trifluoroacetic anhydride, diphenylphosphoric acid azide, diphenylphosphoric acid cyanide and any mixtures thereof.

The amount of the dehydrating agent for condensation is typically about 0.5 mole to about 20 moles, and preferably about 1 mole to about 10 moles, per mole of free 1H-tetrazole-1-acetic acid.

The reaction temperature which can be employed in the preparation of the 1,3,4-thiadiazole-5-thiol esters of Formula (I) may be varied within a wide range of temperatures. In general, the reaction temperature is about −50° C. to about 100° C., and preferably −20° C. to about 50° C.

The reaction of this invention can be conducted, in general, at atmospheric pressure, but it is noted that the pressure employed is not limited thereto. Generally the reaction is conducted in an atmosphere of air. However, it may also be conducted in an atmosphere of an inert gas such as nitrogen, argon and helium.

This reaction are generally conducted in a reaction medium. Any reaction medium which is inactive to the reactants and can dissolve or suspend the reactants can be employed in this invention.

Specific examples of suitable reaction media include dioxane, ethyl acetate, methylene chloride, chloroform, hexane, trifluoroacetic anhydride and aqueous solutions of sodium hydroxide or potassium hydroxide.

The amount of 1H-tetrazole-1-acetic acid or its derivative which can be employed is typically about 1 g to about 50 g, and preferably about 5 g ot about 20 g, per 100 ml of the reaction medium.

After the reaction is substantially completed, the desired compounds of Formula (I) can be recovered from the reaction mixture and purified by the conventional techniques. For example, the reaction medium is evaporated from the reaction mixture and the crude product thus obtained is washed, dried or recrystallized.

The cephalosporin compounds of Formula (II) of this invention can be prepared by reacting 7-aminocephalosporanic acid or its derivative with the 1,3,4-thiadiazole-5-thiol ester of Formula (I).

According to the present process for the preparation of the cephalosporin compounds of Formula (II), the acylation of the 7-position in the 7-aminocephalosporanic acid or its derivative and the substitution of the 3-position in the 7-aminocephalosporanic acid or its derivative proceed selectively in one step to give the desired compounds of Formula (II). Thus, the reaction operation is simple and the recovery of the desired compounds of Formula (II) can be simplified. As a result, the desired compounds of Formula (II) having high purity can be obtained at high yields.

Suitable examples of the derivatives of 7-aminocephalosporanic acid which can be employed in this invention include the salts of alkali metals such as sodium and potassium; the salts of alkaline earth metals such as calcium and magnesium; the salts of nitrogen-containing organic bases such as trimethylamine, triethylamine, pyridine, N-methylpiperidine, N-methylmorpholine; and the esters which can be easily released by catalytic reduction or chemical reduction or under other mild conditions, such as the toluenesulfonylethyl ester, benzyl ester, p-nitrobenzyl ester, phenacyl ester, diphenylmethyl ester, trityl ester, t-butyl ester, an alkyloxymethyl ester such as methoxymethyl ester and ethoxymethyl ester, phenyloxymethyl ester, benzoyloxymethyl ester, acetyloxymethyl ester, 3,5-di(t-butyl)-4-hydroxybenzyl ester, and $\beta,\beta,\beta$-trichloroethyl ester.

The amount of the 1,3,4-thiadiazole-5-thiol ester of Formula (I) which can be employed in the preparation of the cephalosporin compounds of Formula (II) is typically about 0.5 mole to about 2.0 moles, and preferably about 0.9 mole to about 1.2 moles, per mole of 7-aminocephalosporanic acid or its derivative.

The preparation of the cephalosporin compounds of Formula (II) is generally conducted in a reaction medium. Any reaction medium which is inactive to the reactants can be employed in this invention.

Specific examples of suitable reaction media used include water, acetone, dioxane, acetonitrile, toluene, chloroform, methylene chloride, ethylene chloride, tetrahydrofuran, ethyl acetate, formic acid, pyridine, trifluoroacetic acid, N,N-dimethylformamide, methanol, ethanol, methoxy ethanol, diethyl ether, isopropyl ether, N,N-dimethylacetamide, dimethyl sulfoxide and any mixtures of water with the above described organic reaction media.

The amount of 7-aminocephalosporanic acid or its derivative which can be employed is typically about 1 g to about 50 g and preferably about 5 g to about 20 g per 100 ml of the reaction medium.

It is preferred that the reaction between 7-aminocephalosporanic acid or its derivative and the 1,3,4-thiadiazole-5-thiol ester of Formula (I) is conducted at a pH ranging from about 1 to about 9. A more preferred pH is about 3 to about 8.

The temperature of the above described reaction which can be employed in this invention is about $-50°$ C. to about 100° C., and preferably about 0° C. to about 80° C. In general, the above described reaction is carried out at atmospheric pressure, but it is noted that the pressure employed is not limited thereto. The above described reaction may be carried out in an atmosphere of air, and preferably in an atmosphere of an inert gas such as nitrogen, argon and helium.

The above described reaction is continued until the desired compound of Formula (II) is produced in a most appropriate amount. The period of time of the above described reaction typically ranges from about 10 minutes to several tens of hours, and preferably from about 0.5 hour to about 5 hours.

Further, in order to promote the above described reaction of this invention there can be employed a base including an alkali metal hydrogencarbonate such as sodium hydrogencarbonate and potassium hydrogencarbonate, a trialkylamine such as trimethylamine and triethylamine, pyridine; an inorganic acid salt such as a chloride, bromide, iodide, thiocyanate or nitrate of lithium, sodium, potassium or ammonium; a metal compound such as cupric chloride, cupric bromide, cupric fluoride, cupric nitrate, cuprous nitrate, cupric sulfate, cuprous sulfate, cupric borate, copper metaborate, cupric phosphate, cupric cyanide, cuprous cyanide, cupric formate, cuprous formate, cupric acetate, cuprous acetate, copper propionate, copper citrate, cupric tartarate, cuprous tartarate, cupric benzoate, cuprous benzoate, cupric salicylate, cuprous salicylate, ferric chloride, ferrous chloride; a Lewis acid such as titanium tetrachloride, titanium tetrabromide, zirconium tetrachloride, silicon tetrachloride, tin tetrachloride, antimony trichloride, antimony pentachloride, bismuth trichloride, aluminum trichloride, aluminum tribromide, zinc dichloride, boron trifluoride, boron trichloride, boron tribromide; a quaternary ammonium salt such as tetramethylammonium chloride, tetraethylammonium bromide, dimethyldiphenylammonium chloride, triethylbenzylammonium bromide; and a tetraalkylphosphonium halide such as tetramethylphosphonium chloride, tetraethylphosphonium bromide, and tetraphenylphosphonium iodide.

The amount of these compounds which can be employed to promote the above-described reaction typically ranges from about 0.1 mole to about 10 moles, and preferably from about 1 mole to about 5 moles, per mole of 7-aminocephalosporanic acid or its derivative.

The reaction products are separated and collected by the conventional methods from the reaction mixture and the cephalosporin compounds of Formula (II) of this invention can be isolated either as such or in the form of the salts or the esters. When the cephalosporin compounds of Formula (II) are obtained in the form of the esters, the esters can be converted into the cephalosporin compounds by catalytic reduction or chemical reduction or under other mild conditions.

The cephalosporin compounds of Formula (II) thus obtained can be converted, by the conventional methods, into the salts of an alkali metal such as sodium and potassium; the salt of ammonium; the salts of an alkaline earth metal such as magnesium and calcium; and the salts of diphenylenediamine, dicyclohexylamine, dibenzylethylenediamine, triethylamine, tri-n-butylamine, triphenylamine, triallylamine, dibenzylamine, N,N-dibenzylaminoethanol, procaine, quinine, 2-methylquinoline, 2-amino-5-nitrothiazole, 9-aminoacridine or guanylurea. These salts exhibit excellent features for preparing medicaments, for example, from the view point of their water solubility.

The cephalosporin compounds of Formula (II) are useful as antimicrobial agents.

The following Examples are given to illustrate the present invention more specifically. However, it should be understood that the invention is in no way limited by these Examples.

EXAMPLE 1

In 20 ml of trifluoroacetic anhydride were suspended 1.3 g of 1H-tetrazole-1-acetic acid and stirred at 20° C. for 15 minutes. Then the trifluoroacetic anhydride and by-products were distilled off under reduced pressure, and to the residue was added a mixed solution of 1.3 g of 2-methyl-1,3,4-thiadiazole-5-thiol and 50 ml of ethyl acetate and stirred at 20° C. for 3 hours. The solution thus obtained was condensed to dryness to give 3.8 g of a solid, and the solid was dissolved in a small amount of ethyl acetate, and then were added 20 ml of petroleum ether thereto. The precipitate thus formed was collected by filtration and dried to give 2.40 g of 1H-tetrazole-1-acetic acid 2-methyl-1,3,4-thiadiazol-5-ylthiol ester the form of yellowish powder at a yield of 99%.

Elemental Analysis Values:
Calculated (%): C, 29.8; H, 2.5; N, 34.7; S, 26.4. Found (%): C, 29.9; H, 2.5; N, 34.5; S, 26.6.

Infrared Absorption Spectrum:
$\gamma_{c=o}$: 1762 cm$^{-1}$

NMR Spectrum (CDCl$_3$), $\delta$ppm:
2.58 (s, 3H), 5.95 (s, 2H), 8.95 (s, 1H)

Ultraviolet Absorption Spectrum (in ethyl acetate):
$\lambda_{max}$ = 323 m$\mu$

EXAMPLE 2

The same procedure as in Example 1 was repeated except that 1.2 g of 1,3,4-thiadiazole-5-thiol were used instead of the 1.3 g of 2-methyl-1,3,4-triadiazole-5-thiol. As a result, 2.2 g of 1H-tetrazole1-acetic acid 1,3,4-thiadiazol-5-ylthiol ester were obtained in the form of yellowish powder.

Elemental Analysis Values:
Calculated (%): C, 26.3; H, 1.8; N, 36.8; S, 28.1. Found (%): C, 26.5; H, 1.8; N, 36.5; S, 28.3.

Infrared Absorption Spectrum:
$\gamma_{c=o}$: 1765 cm$^{-1}$

EXAMPLE 3

In 100 ml of ethyl acetate were dissolved 1.3 g of 2-methyl-1,3,4-thiazole-5-thiol and then 1.3 g of 1H-tetrazole-1-acetic acid with stirring, followed by a further addition of 2.06 g of dicyclohexylcarbodiimide with stirring under cooling with ice. The mixture was stirred under cooling with ice for 4 hours and left to stand at 0° C. for 20 hours. Then the precipitate of dicyclohexylurea was separated by filtration and the filtrate was washed twice with 30 ml of saturated sodium chloride aqueous solution and dehydrated with anhydrous magnesium sulfate, and subsequently ethyl acetate was distilled at 25° C. under reduced pressure. The residue was dissolved in a small amount of ethyl acetate, and addition of 20 ml of petroleum ether thereto resulted in the formation of precipitates. The precipitates were collected by filtration and dried to give 2.26 g of 1H-tetrazole-1-acetic acid 2-methyl-1,3,4-thiadiazol-5-ylthiol ester at a yield of 93.4%. The analytical values of this product were the same as those of Example 1.

EXAMPLE 4

In 20 ml of methylene chloride were dissolved 8 ml of trimethylaluminum solution having 2.5 mol concentration in hexane and cooled to 0° C. To the solution were added 2.6 g of 2-methyl-1,3,4-thiadiazole-5-thiol at 0° C. and the reaction was continued at 25° C. for 2.5 hours in a nitrogen atmosphere with stirring. Then to the solution were added 1.4 g of 1H-tetrazole-1-acetic acid methyl ester and the reaction was continued at 25° C. for 6 hours with stirring. The reaction medium and unreacted substances were distilled from the reaction solution under reduced pressure and to the residue thus obtained were added 50 ml of ethyl acetate and insoluble materials were removed by filtration. Addition of 50 ml of petroleum ether to the filtrate resulted in the precipitation of solids and the solids were collected by filtration and dried to give 2.31 g of 1H-tetrazole-1-acetic acid 2-methyl-1,3,4-thiadiazol-5-ylthiol ester at a yield of 95%. The analytical values of the product were the same as those of Example 1.

EXAMPLE 5

The same procedure as in Example 4 was repeated except that 1.56 g of 1H-tetrazole-1-acetic acid ethyl ester were used instead of the 1.4 g of 1H-tetrazole-1-acetic acid methyl ester. As a result, 2.35 g of the same 1H-tetrazole-1-acetic acid 2-methyl-1,3,4-thiazol-5-ylthiol ester as in Example 4 were obtained at a yield of 97%.

EXAMPLE 6

To a solution of 1.4 g of 7-aminocephalosporanic acid, 0.4 g of sodium bicarbonate and 60 ml of water was added a solution of 1.2 g of the 1H-tetrazole-1-acetic acid 2-methyl-1,3,4-thiadiazol-5-ylthiol ester as obtained in Example 1 and 10 ml of acetone with stirring. The mixed solution thus obtained was further stirred at 60° C. for 4 hours in a nitrogen atmosphere while adjusting the pH of the solution to 6.4 with a 3% sodium bicarbonate aqueous solution. After completion of the reaction acetone was distilled from the reaction solution under reduced pressure, and the water layer was washed twice with 50 ml of ether. Then the pH of the water layer was adjusted to 3 with 3 N hydrochloric acid and the water layer was extracted three times with 100 ml of ethyl acetate. Then the extract was dried over sodium sulfate, and the reaction medium was distilled to give 2.2 g of 7-(1H-tetrazol-5-ylacetamide)-3-(2-methyl-1,3,4-thiadiazol-5-ylthiomethyl)-3-cephem-4-carboxylic acid having a purity of 93.5% at a yield of 90.6%.

Ultraviolet Absorption Spectrum (in 3% sodium hydrogencarbonate aqueous solution):
$\lambda_{max}$ = 272 m$\mu$ In 100 ml of an aqueous solution containing 0.1 M sodium acetate and 0.2 M sodium chloride were dissolved 1.44 g of the above described cephalosporin compound and the pH of the solution was adjusted to 4.5 with acetic acid. The solution thus prepared was flowed in a 150 ml column packed with Amberlite XAD-2 (manufactured by Rohm & Haas Co., Ltd.) to adsorb a desired product thereon. After washing with 3 l of a 5% acetic acid aqueous solution and further with 750 ml of water, the product was dissolved in a 50% acetone aqueous solution and the solution containing the desired product was freeze-dried to give 1.22 g of purified 7-(1H-tetrazol-1-ylacetamide)-3-(2-methyl-1,3,4-thiadiazol-5-ylthiomethyl)-3-cephem-4-carboxylic acid having a purity of 99.1%.

Ultraviolet Absorption Spectrum (in 3% sodium bicarbonate aqueous solution):

$\lambda_{max} = 272$ mµ

Melting Point: 197° C.-200° C. (Decomp.)

NMR Spectrum (DMSO-d$_6$), δppm:

2.68 (s, 3H), 3.71 (dd, 2H), 4.39 (dd, 2H), 5.12 (d, 1H), 5.37 (s, 2H), 5.73 (q, 1H), 9.33 (s, 1H), 9.49 (d, 2H).

In 2 ml of water were dissolved 0.92 g of the compound having a purity of 99.1% thus obtained and 0.17 g of sodium bicarbonate and the solution was filtered. To the filtrate were added 9 ml of 99% ethanol, and a crystal of sodium 7-(1H-tetrazol-1-ylacetamido)-3-(2-methyl-1,3,4-thiadiazol-5-ylthiomethyl)-3-cephem-4-carboxylate was collected by filtration.

Ultraviolet Absorption Spectrum (in 3% sodium bicarbonate aqueous solution):

$\lambda_{max} = 272$ mµ

NMR Spectrum (DMSO-d$_6$), δppm:

2.70 (s, 3H), 3.67 (dd, 2H), 4.57 (dd, 2H), 5.08 (d, 1H), 5.47 (s, 2H), 5.65 (q, 1H), 9.50 (s, 1H), 9.72 (d, 2H)

EXAMPLE 7

The same procedure as in Example 6 was repeated except that 1.1 g of the 1H-tetrazole-1-acetic acid 1,3,4-thiadiazol-5-ylthiol ester as obtained in Example 2 were used instead of the 1.2 g of 1H-tetrazole-1-acetic acid 2-methyl-1,3,4-thiadiazol-5-ylthiol ester. As a result, 2.1 g of 7-(1H-tetrazol-1-ylacetamido)-3-(1,3,4-thiadiazol-5-ylthiomethyl)-3-cephem-4-carboxylic acid having a purity of 93.1% were obtained at a yield of 88.9%.

1 g of this compound was recrystallized from a 50% acetone aqueous solution to give 0.55 g of a purified crystal having a melting point of 155° C. (decomp.) and a purity of 98.5%.

Ultraviolet Absorption Spectrum (3% sodium hydrogencarbonate aqueous solution): $\lambda_{max} = 273$ mµ

EXAMPLE 8

To a solution of 1.4 g of 7-aminocephalosporanic acid, 30 ml of N,N-dimethylformamide and 30 ml of water was added a solution of 1.2 g of 1H-tetrazole-1-acetic acid 2-methyl-1,3,4-thiadiazol-5-ylthiol ester, 5 ml of N,N-dimethylformamide and 5 ml of water with stirring and the mixed solution thus obtained was further stirred at 60° C. for 4 hour in a nitrogen atmosphere. After completion of the reaction the N,N-dimethylformamide and water were distilled from the reaction solution, and to the residue were added 50 ml of water and 100 ml of ethyl acetate. The pH of the solution thus obtained was adjusted to 3 with 3 N hydrochloric acid and then the solution was extracted with ethyl acetate and further twice with 100 ml of ethyl acetate. The extract was dried over sodium sulfate and the ethyl acetate was distilled to give 2.16 g of 7-(1H-tetrazol-1-ylacetamido)-3-(2-methyl-1,3,4-thiadiazol-5-ylthiomethyl)-3-cephem-4-carboxylic acid having a purity of 92.5% at a yield of 89.0%. The analytical values of this product was found to be in agreement with those of the product in Example 6.

While the invention has been described in detail and with reference to specific embodiments thereof, it will be apparent to one skilled in the art that various changes and modifications can be made therein without deparmtent from the spirit and scope thereof.

What is claimed is:

1. An 1,3,4-thiadiazole-5-thiol ester of the formula,

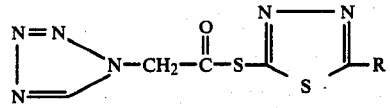

wherein R is a hydrogen atom or a methyl group.

2. The 1,3,4-thiadiazole-5-thiol ester of claim 1, wherein R is a hydrogen atom.

3. The 1,3,4-thiadiazole-5-thiol ester of claim 1, wherein R is a methyl group.